United States Patent [19]

Vlock

[11] 4,365,958

[45] Dec. 28, 1982

[54] COMBINED DENTAL DRILL AND ANCHOR PIN

[76] Inventor: David G. Vlock, New York, N.Y.

[21] Appl. No.: 274,834

[22] Filed: Jun. 17, 1981

[51] Int. Cl.³ .............................................. A61C 5/08
[52] U.S. Cl. .................................................... 433/225
[58] Field of Search ....................... 433/225, 220, 174; 411/387, 420, 421

[56] References Cited

U.S. PATENT DOCUMENTS 4,187,611  2/1980  Chan .................................... 433/225
4,219,620  8/1980  Carse ................................... 433/225

Primary Examiner—Robert Peshock
Attorney, Agent, or Firm—Lawrence Rosen

[57] ABSTRACT

A combined dental drill and anchor pin for use in the field of denistry. Restoration techniques, involving the use of anchor pins for the retention and reinforcing of dental support structures as well as for various mechanical appliances used in the field of orthodontics, are facilitated by combining the drill and anchor pin in a single structure thereby eliminating separate drilling and pin insertion steps.

6 Claims, 3 Drawing Figures

COMBINED DENTAL DRILL AND ANCHOR PIN

FIELD OF THE INVENTION

The present invention relates to a novel dental appliance, more particularly the invention pertains to a combined dental drill and anchor pin for use in teeth restoration and orthodontic procedures.

BACKGROUND OF THE INVENTION

In conventional dentistry procedures it is customary to install one or more pins into broken down teeth or into teeth to which orthodontic appliances are being applied. The treatment of broken down teeth is of course more prevalent, and the present invention will be discussed primarily in conjunction with restorative techniques for treating teeth where the nerve is still alive. It will be understood, however, that the invention is also applicable to orthodontic techniques or to non-vital teeth.

As is well known, the conventional procedure is to initially drill one or more relatively deep holes in the dentin portion of the tooth undergoing repair. The drilling can be carried out, for example, by utilizing a typical dental twist drill. The dentist then screws in a small, screw-threaded anchor into each of the holes leaving a portion of the screw-threaded pin sticking out of the hole. The remainder of the screw-threaded pin is retained in the dentin as the anchor.

Illustrative U.S. patents pertaining to anchor retention pins include the following:
  Baker—U.S. Pat. No. 3,364,575
  Tieche—U.S. Pat. No. 4,142,293
  Chan—U.S. Pat. No. 4,187,611
  Smith—U.S. Pat. No. 4,189,834
  Weissman—U.S. Pat. No. 4,202,101
  Carse—U.S. Pat. No. 4,219,620
A commercially available screw pin is sold by Pulpdent Corporation of America as "Stabilok" screw-pins under U.S. Pat. No. 4,189,834.

A number of commercially available dental drills have been employed for making the holes or channels in the dentin which are required for the anchor pins.

In accordance with present day practices, therefore, two instruments are needed: a drill, e.g. a twist drill; and a diameter-coordinated screw pin. After the twist drill digs its deep hole or channel, the path of insertion must again be found in order to screw in the screw-threaded anchor pin. Since the drilled hole is very tiny, in general being on the order of 0.021 inch or so, plus or minus a few ten thousandths of an inch in diameter. If the screw-threaded pin is not inserted with its long axis exactly parallel and in line with the orifice and the long axis of the hole, it is difficult, if not impossible, to successfully screw the pin into the hole. Moreover, sometimes the drilled hole or opening is in a difficult location for good accessibility or visibility. At times, the drilled hole or channel is obfuscated by debris or saliva.

OBJECTS OF THE INVENTION

One object of the present invention is to provide means for readily anchoring a pin in a tooth for building superstructures on broken or undermined dentition.

Another object of the present invention is to provide means which facilitate the positioning of reconstruction or reinforcing pins in teeth.

A further object of the present invention is to provide means for anchoring a pin which eliminates the need to use separate equipment for initially drilling a hole and then for inserting the pin therein as well as eliminating the separate and distinct drilling and insertion steps.

A still further object of the present invention is to provide dental equipment for anchoring pins which avoids the disadvantages of the present apparatus and procedures.

These and other objects will become more readily apparent from the ensuing description and illustrative embodiments of the present invention.

SUMMARY OF THE INVENTION

According to the invention, a drill and an anchor pin are combined in one structure. In general, the overall instrument or device of this invention has at its end a short drill, e.g. a twist drill, immediately followed by an anchor pin section, a major portion of which will generally protrude above the surface of the dentin and which will serve as the retaining or reinforcing device for enhancing the attachment of an amalgam filling or other restorative material to the tooth. In order to limit the drilling depth a stop means is positioned on the shank carrying the drill bit and the anchor pin. Furthermore, the device is provided with a weakened point, i.e. a frangible reduced portion, or shearing joint positioned on the shank immediately following the desired protruding length of anchor pin.

BRIEF DESCRIPTION OF THE DRAWINGS

The invention will be more fully understood by reference to the accompanying drawings in which.

DETAILED DESCRIPTION OF THE INVENTION

Figure 1:
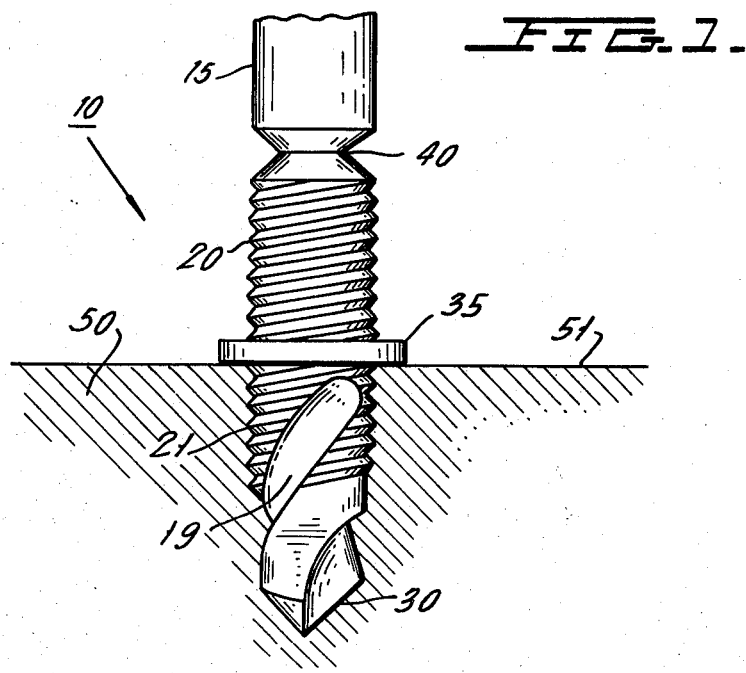
FIG. 1 is a partly cut away side view showing the combined drill and anchor pin device according to the present invention.

Referring now to the drawings and more specifically to FIG. 1, the present invention comprises a combined drill and anchor pin structure 10, which may be a latch type or straight hand piece bur shank made of stainless steel, plated cast iron or any material harder than dentin and suitable for making a drill therefrom; has a trailing shank portion 15, an anchor pin 20, a screw threaded portion 21, a groove 19 for debris removal and a drill 30. A stop 35, which may be a part of anchor pin 20, is positioned so that it separates the drill 30 and a portion of the screw threaded pin from the protruding portion of the anchor pin 20. After drill 30 has pierced the dentin section 50 of the tooth to the desired depth, the stop 35 will come to rest on the top surface 51 of dentin 50 and further drilling will cease.

Figure 2:
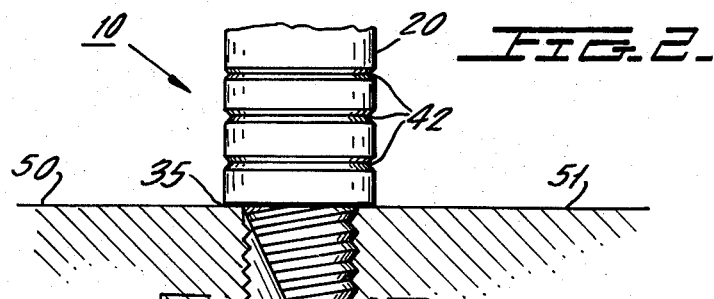
FIG. 2 is a partly cut away side view showing several variations on the combined drill and anchor pin device according to the present invention.

The drill 30 used in the instrument of this invention may be any kind of deep drilling end such as a single flute, a twist drill, and the like for drilling deep pin holes. For many purposes the drill 30 can be a conventional twist drill type. FIG. 1 shows a twist drill while a single flute drill is illustrated in FIG. 2. Portion 21 of the anchor pin secures the anchor pin to the tooth and portion 21 must have a screw thread for the present purposes. The protruding section or portion of anchor pin 20 can be screw threaded as shown in FIG. 1 or can be a straight shank that has been scored or provided with grooves 42 to enhance its functioning as a retention or reinforcing pin. In general, the anchor pin section of the present instrument is screw threaded, and it will have an overall length of from about 3 to 6 mm. For most restorative dental work, the segment of the anchor pin extending above or protruding from dentin surface 51 will range from about 1.5 to 4 mm. The outside diameter or lands or anchor screw portion 21 must be slightly larger than the diameter of drill 30, while the grooves of the anchor screw pin 21 must be slightly smaller than the diameter of drill 30. Useful diameters of the anchor pin and the drill will range from about 0.017 to 0.028 inches. It will be understood however, that for some purposes the diameter of that portion of the anchor pin protruding from the dentinal surface may be less or greater than the diameter of the drill 30.

As also shown in FIG. 1, the trailing shank 15 has a reduced diameter or shearing joint 40 positioned on the upper end of the anchor pin 20 so as to provide a fracture or shear point. When rotation continues following abutment of the stop 35 against the upper dentin surface 51, shearing joint 40 severs under continuing torsional forces leaving the drill 30 and anchor pin portion 21 securely affixed in dentin 50, and that portion of the anchor pin 20 below shearing joint 40 protruding from dentin surface 51.

Figure 3:
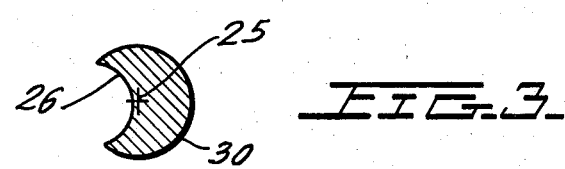
FIG. 3 is an end view of the single fluted drill illustrated in FIG. 2.

In FIG. 3 the centerpoint 25 and the cutting edge 26 of the drill are shown. The drill may have single or multiple blades, as desired.

Although the use of an instrument having a shearing joint 40 is preferred under the invention it will be understood that other arrangements are also possible. Thus, the trailing shank may be cooperatively attached to an elongated circular-cylindrical shank (not shown) which in turn is attached to a latching-type dental hand piece (not shown). In such a structure, the trailing shank, which can also function as a part of the protruding anchor pin, is detached from the dental handpiece (not shown) when stop 35 is in abutment with the upper dentinal surface 51. It will also be understood that the free end of the trailing shank may have a variety of shapes to cooperate with some locking means on a dental handpiece so that the essential structure of the present invention is locked to a powered dental handpiece.

As will be comprehended by those skilled in the art, the combined drill and pin instrument of this invention may be used in a variety of orientations at various inclinations and inverted from the position shown in the drawings, so that certain positional terms in the foregoing description are used to describe the relative portions of the combined structure without limitation to their orientation with respect to a horizontal plane.

In addition, those skilled in the art will appreciate that a wide variety of structures may be devised within the broad concept of the present invention, and that the invention is not limited solely to the disclosed embodiments but is subject to variations and modifications without departing from the inventive concepts.

What is claimed is:

1. A dental device combining a drilling end with an anchor pin for the purpose of performing in a single step drilling a pin hole in tooth dentin and retaining the anchor pin within the tooth structure; which comprises a drill, positioned at one end thereof, an integrally connected anchoring pin, stop means positioned on said anchoring pin, and a trailing shank at the other end for attaching said combined drill-anchoring pin device to a powered dental hand piece wherein said trailing shank is provided with a shearing point adjacent to the protruding portion of the anchor pin, which is scored or grooved, so as to eliminate damaging the tooth when the stop means is adjacent to the tooth.

2. The combined drill-anchoring pin device of claim 1 wherein said anchoring pin is screw threaded.

3. The combined drill-anchoring pin device of claim 1 wherein said drill is a twist drill.

4. The combined drill-anchoring pin device of claim 1 wherein said drill is a single or multiple fluted end cutting drill.

5. The combined drill-anchoring pin device of claim 1 wherein said trailing shank is releasably attached to the powered dental handpiece, and when released the trailing shank serves as a portion of the protruding anchoring pin.

6. The combined drill-anchoring pin device of claims 1 or 2 wherein said stop means is positioned between said screw retention section and said protruding section of the anchoring pin.

* * * * *